(12) United States Patent
Radziuk et al.

(10) Patent No.: US 6,222,626 B1
(45) Date of Patent: *Apr. 24, 2001

(54) ATOMIC ABSORPTION SPECTROMETER

(75) Inventors: Bernhard Radziuk, Frickingen; Günter Rödel, Owingen, both of (DE)

(73) Assignee: Bodenseewerk Perkin-Elmer GmbH (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/141,543

(22) Filed: Aug. 28, 1998

(30) Foreign Application Priority Data

Sep. 12, 1997 (DE) ............................. 197 40 210

(51) Int. Cl.[7] ....................................... G01J 3/42
(52) U.S. Cl. ..................... 356/307; 356/319; 356/312; 356/315
(58) Field of Search ..................... 356/307, 311, 356/312, 315, 316, 319, 326, 328

(56) References Cited

U.S. PATENT DOCUMENTS

| | | |
|---|---|---|
| 4,508,451 | 4/1985 | Stockdale. |
| 4,545,680 * | 10/1985 | Smith, Jr.. |
| 5,018,856 * | 5/1991 | Harnly et al.. |
| 5,042,946 * | 8/1991 | Harada. |
| 5,181,077 * | 1/1993 | Dencks et al.. |
| 5,311,277 * | 5/1994 | Sasaki et al.. |
| 5,608,526 | 3/1997 | Piwonka-Corle et al.. |

FOREIGN PATENT DOCUMENTS

| | | |
|---|---|---|
| 2207298 | 9/1972 | (DE). |
| 2539184 | 3/1976 | (DE). |
| 3939148 | 5/1991 | (DE). |
| 19543729 | 5/1997 | (DE). |

OTHER PUBLICATIONS

Liger; "Diodehaser Atomic Absorption . . . Technique" Spectrochimica Acta Part B 52 1997 1125–1138.*

* cited by examiner

Primary Examiner—F L. Evans
(74) Attorney, Agent, or Firm—St. Onge Steward Johnston & Reens LLC

(57) ABSTRACT

The invention relates to an atomic absorption spectrometer, comprising a measuring light path leading from at least one light source emitting line radiation corresponding to at least one element to be detected, through an atomization means for atomizing a sample containing the element to be detected, to a detection means, and a reference light path leading from each light source to the detection means. The invention is characterized in that a beam splitting means is provided such that a first component of the line radiation of each light source is guidable via the measuring light path and a second component of the line radiation of each light source is simultaneously guidable via the reference light path.

21 Claims, 12 Drawing Sheets

ATOMIC ABSORPTION SPECTROMETER

TECHNICAL FIELD

The invention relates to an atomic absorption spectrometer, comprising a measuring light path, leading from at least one light source emitting a line radiation corresponding to at least one element to be detected, through an atomization means for atomizing a sample containing the at least one element to be detected, to a detection means and a reference light path from each light source to the detection means.

Further, the invention relates to a method comprising the steps of coupling radiation of at least one light source emitting line radiation of at least one element to be detected into a measuring light path, leading from each light source through an atomization means for atomizing a sample containing the element to be detected, to a detecting means, coupling of radiation of each light source into a reference light path, leading from each light source to the detection means, measuring the intensity of the radiation passed through the measuring light path, measuring the intensity of the radiation passed through the reference light path, determining the radiation absorbed by the atomized sample from the intensity of the radiation passed through the measuring light path and the intensity of the radiation passed through the reference light path.

BACKGROUND ART

Such atomic absorption spectrometer and such method are known in the prior art.

FIG. 5 schematically shows an atomic absorption spectrometer 500 in accordance with the prior art. The atomic absorption spectrometer 500 comprises a measuring light path 510 and a reference light path 520. Further, the atomic absorption spectrometer 500 is provided with a light source 550 emitting a line radiation corresponding to an element to be detected, said element being contained in a sample to be examined.

The light emitted by the light source is coupled, by a chopper means 590, into either the measuring light path 510 of the reference light path 520. The coupling is in accordance with the position of the elements being provided in the chopper means (not shown).

In FIG. 5a, the light path is shown for a first position of the elements of the chopper means 590. In this position, the light emitted from the light source is coupled into the measuring light path 510. Accordingly, the reference light path 520 is represented by a dashed line.

The light emitted from the light source travels on the measuring light path 510 through an atomization means 560 in which the sample to be examined is atomized. In FIG. 5, the atomization means 560 is only shown schematically. In dependency on the sample matrix and the element contained in the sample, all atomization means known in the field of atomic absorption spectroscopy, as for example atomization furnace, flame, cold vapor cell and the like, can be used.

After passing through the atomization means 560, the radiation impinges on a detector device 530, for measuring the intensity of the radiation.

In FIG. 5b, the light path is shown for a second position of the elements of the chopper means 590. In this position, the light emitted from the light source is coupled into the reference light path 520. In accordance with FIG. 5a, the measuring light path 510 is shown in dashed line in FIG. 5b.

Using the reference light path 510, the line radiation emitted from the light source impinges directly onto the detector 530 for measuring the intensity of the radiation.

Beside the above described components, the atomic absorption spectrometer 500 comprises optical elements 511 and 521, for example, mirrors and/or lenses. These optical elements are, if need be, for focusing and redirecting the light paths.

In the following, a method for performing a double-beam atomic absorption spectroscopy with the atomic absorption spectrometer of FIG. 5 will be described. With this, reference is made to FIG. 14, representing a time sequence of the method.

After the sample has been atomized in the atomization means 560, line radiation from the light source is coupled in accordance with the respective position of the elements of the chopper means (see FIG. 5A), into the measuring light path 510 for a predetermined time $T_T$ during a first phase P of a measuring cycle C, and the intensity of the radiation passed through the measuring light path 510 is measured in the detector device 530.

After completion of this measurement, radiation emitted by the light source is coupled for a predetermined time $T_R$ into the reference light path due to the respective position of the chopper means (see FIG. 5b). The intensity of the radiation path through the reference light path is detected in the detector device 430.

Finally, the radiation absorbed by the atomized sample is determined from the intensity of the radiation passed through the measuring light path and the intensity passed through the reference light path.

The measuring cycle shown in FIG. 14 is repeatedly performed in order to improve the statistics, in particular, if the atomic absorption is constant over a range which is larger compared to the measuring time. The case of these slowly running processes is particularly seen in the absorption with a flame or a cold vapor cell.

For fast running processes, as for example the atomization in an atomization furnace, the measurements can be, instead of averaging, time dependently recorded. Thus, with the above described spectrometer and respective methods, it is possible to perform an atomic absorption spectroscopy with time resolution.

The disadvantage of the above described spectrometer and the method is the loss of measuring time due to performing the reference measurement, i.e. the second phase R of the measuring cycle T. This is particularly critical in an atomization with an atomization furnace, since the available measuring time is generally very short.

SUMMARY OF THE INVENTION

In view of this, it is the objective problem underlying the invention to improve the prior art spectrometer and the prior art method for performing a doublebeam atomic absorption.

This objective problem is achieved by an atomic absorption spectrometer of the above mentioned kind, which is distinguished in that a beam splitting means is provided such that a first component of the line radiation of each light source is guidable via the measuring light and a second component of the line radiation of each light source is simultaneously guidable via the reference light path.

Via the beam dividing means, the line radiation from the light source can be divided, and thus, coupled simultaneously into both the measuring light path and the reference light path. Therefore, it is possible to simultaneously perform the sample measurement and the reference measurement. As a consequence, the available measuring time can be considerably increased. For the case that the time $T_T$ and $T_R$ for the sample measurement and the reference measurement are set equal, a doubling of the available measuring time results.

For the case that the time $T_T$ and $T_R$ are set differently, the increase of additional measuring time is given by the smaller of the two time intervals.

With this, the detection means may comprise a first detector device for detecting the first component of the line radiation (measuring light) and a second detector for detecting the second component of the line radiation (reference light).

This embodiment has the advantage, that a known atomic absorption spectrometer, as for example shown in FIG. 5, can be easily modernized.

In accordance with a preferred embodiment, the atomic absorption spectrometer in accordance with the invention comprises a detection means having a single detector, being provided with at least two sections, the first section being for detecting the first component of the line radiation and the second section being for detecting the second component of the line radiation. It is an advantage of this embodiment that only one detector has to be provided, and therefore, the detector means can be formed considerably smaller and with less costs.

The detector device or the detector devices can be provided in form of semiconductor detector devices, for example using photodiode or CCD structures.

In the atomic absorption spectrometer of the invention, all line radiation emitting sources being known in the field of atomic absorption can be employed, for example hollow cathode lamps or electrodeless discharge lamps.

In front of the detector or of each of the detectors, a monochromator means can be provided.

In accordance with a preferred embodiment, the monochromator means can comprise an entrance slit, the first and the second component of the line radiation being imaged onto the entrance slit separated from each other in longitudinal direction of the entrance slit. With this arrangement, a simple detector arrangement can be realized.

Preferably, the second component of the line radiation can be guided between the beam divider means and the entrance slit with a light guiding means, for example a fiber connection. By doing so, it is avoided that, besides the measuring light path, also another light path has to be formed by optical elements, as for example by mirrors and/or lenses. Thus, and since optical elements are avoided in the reference light path, no adjustment of optical elements in the reference light path is necessary, simplifying the overall adjustment of the atomic absorption spectrometer. Further, by using a light guiding connection, the reference light path can be provided more flexible in the atomic absorption spectrometer. Thereby, the atomic absorption spectrometer can be formed comparably smaller.

Instead of a monochromator means, one or more polychromators, preferably in connection with CCD detectors or a photodiode array, can be used in the atomic absorption spectrometer. Thus, moveable parts, as they are provided in known monochromators, can be avoided. Therefore, an additional adjusting, as it is for example necessary when using a monochromator, can be avoided. In the atomic absorption spectrometer in accordance with the invention, all atomizing means known in the field of atomic absorption can be used, as for example an atomization furnace, a flame or a cold vapor cell.

In accordance with a preferred embodiment, the atomization means can comprise an atomization furnace and/or a flame and/or a cold vapor cell, which can be introduced selectively into the measuring light path. Such an atomic absorption spectrometer has the advantage that it can be directly used for a variety of applications without having to rearrange the spectrometer.

Preferably, the different atomization means can be provided such that the introduction into the measuring light path can be automized, for example using a microprocessor control. With such an arrangement, the atomic absorption measurements can be automatically performed by respectively programming the processor.

In accordance with a further embodiment of the invention, the atomic absorption spectrometer can comprise a continuum light source, for example a D2-lamp, such that, by means of the beam divider, a first component of the continuum radiation of the light source can be coupled into the measuring light path, and a second component of the continuum radiation of the light source can be coupled into the reference light path. With this arrangement, it is possible to perform a sample measurement as well as a reference measurement with the continuum light source. With these two measurements, it is possible to perform a background compensation or background correction of the atomic absorption measurements.

Further, in accordance with a preferred embodiment, the intensities of each light source can be controllable with respect to time. Thus, it is possible to realize a given measuring cycle by changing the intensities of the line radiation or the line radiation and the continuum radiation. Furthermore, the most favorable signal to noise ratios can be set for a given application.

Additionally, the objective problem underlying the invention is achieved by a method for performing a double-beam atomic absorption of the above mentioned kind, which is distinguished in that the coupling of the radiation into the measuring light path and into the reference light path and the measuring of the intensity of the radiation passed through the measuring light path and the measuring of the radiation passed through the reference light path are performed simultaneously.

By simultaneously measuring the radiation passed through the measuring light path and the reference light path, the measuring time loss occurring in a double-beam atomic absorption due to the reference measurement following after the sample measurement, can be avoided. Therefore, considerably more measurements can be obtained in the same time, improving the signal to noise ratio.

As a consequence, and on the one hand, the time resolution can be increased, when performing spectroscopy with time resolution.

On the other hand, using this method, accurate results can be obtained particularly in connection with fast running atomization processes.

In accordance with a particularly advantageous embodiment, the method in accordance with the invention further comprises the steps of simultaneously coupling radiation from a continuum light source into the measuring light path and into the reference light path, simultaneously measuring the intensity of the continuum radiation passed through the measuring light path and of the intensity of the continuum radiation passed through the reference light path, determining the radiation absorbed by the atomized sample from the intensity of the continuum radiation passed through the measuring light path and the intensity of the continuum radiation passed through the reference light path, correcting the line radiation absorbed by the sample taking the background radiation absorbed by the sample into consideration.

Simultaneously measuring the intensity of the line radiation and simultaneously measuring the intensity of the continuum radiation can be performed in accordance with a measuring cycle, comprising a measurement of the continuum radiation and measurement of the line radiation.

With this, the measuring time for the measurement of the continuum radiation and the measuring time for the measurement of the line radiation can be set dependent on the used atomization processes, the intensity of the line radiation light source and the intensity of the continuum radiation light source, as well as on the changing rate of the background absorption.

Due to this flexible process control, the respective measuring time can be optimized with respect to the specific form of atomic absorption, being necessary for detecting a specific element, whereby the most favorable signal to noise ratio is taken into consideration.

In a preferred embodiment of the method, a phase can be provided in which the radiation emitted by the atomization means is measured. During such phases, in the following referred to as dark phases, radiation is neither emitted by the light source emitting line radiation nor by the line source emitting line radiation or the light source emitting continuum radiation.

By measuring the so called dark phases, the absorption measurement can be corrected with respect to the radiation emitted by the atomization means. In the case of an atomization furnace or a flame, such a radiation is emitted in form of temperature radiation. Furthermore, such a radiation can be produced by spontaneous emission or similar physical processes of the matter being employed. By taking this radiation into consideration, an influence of the atomization means on the absorption measurement can be corrected. Summarized, the accuracy of the measurement can be increased.

Simultaneously measuring the intensity of the line radiation, simultaneously measuring the intensity of the continuum radiation and measuring the intensity of the radiation emitted by the atomization means, can be advantageously performed in accordance with a measuring cycle, comprising a first measurement of the radiation emitted by the atomization means, a first measurement of the continuum radiation, a second measurement of the radiation emitted by the atomization means, a measurement of the line radiation, a third measurement of the radiation emitted by the atomization means, and a second measurement of the continuum radiation.

Preferably, the measuring time for the first measurement of the radiation emitted by the atomization means, the measuring time for the first measurement of the continuum radiation, the measuring time for the second measurement of the radiation emitted by the atomization means, the measuring time for the measurement of the line radiation, the measuring time for the third measurement of the radiation emitted by the atomization means, and the measuring time for the second measurement of the continuum radiation can be set dependent on the used atomization process, on the intensity of the line radiation emitting light source and the intensity of the continuum radiation emitting light source, the intensity of the light source produced by the atomization means, as well as on the changing rate of the background absorption.

Due to this advantageous arrangement, the above discussed advantages with respect to a flexible time controlling can be obtained. Furthermore, in such a flexible time control in accordance with the invention, the radiation emitted by the atomization means can be taken into consideration. In particular, and in dependency on the thermal behavior of the atomization furnace, a measuring cycle can be selected which optimizes the dark phases and the correction of the atomic absorption measurement, i.e. to obtain a correction as accurate as possible with dark phases as short as possible.

BRIEF DESCRIPTION OF THE DRAWINGS

Further advantages of the invention will result from the explanatory description of preferred embodiments of the invention, referring to the drawings, in which.

DETAILED DESCRIPTION OF THE PREFERRED EMBODIMENTS

Figure 1:
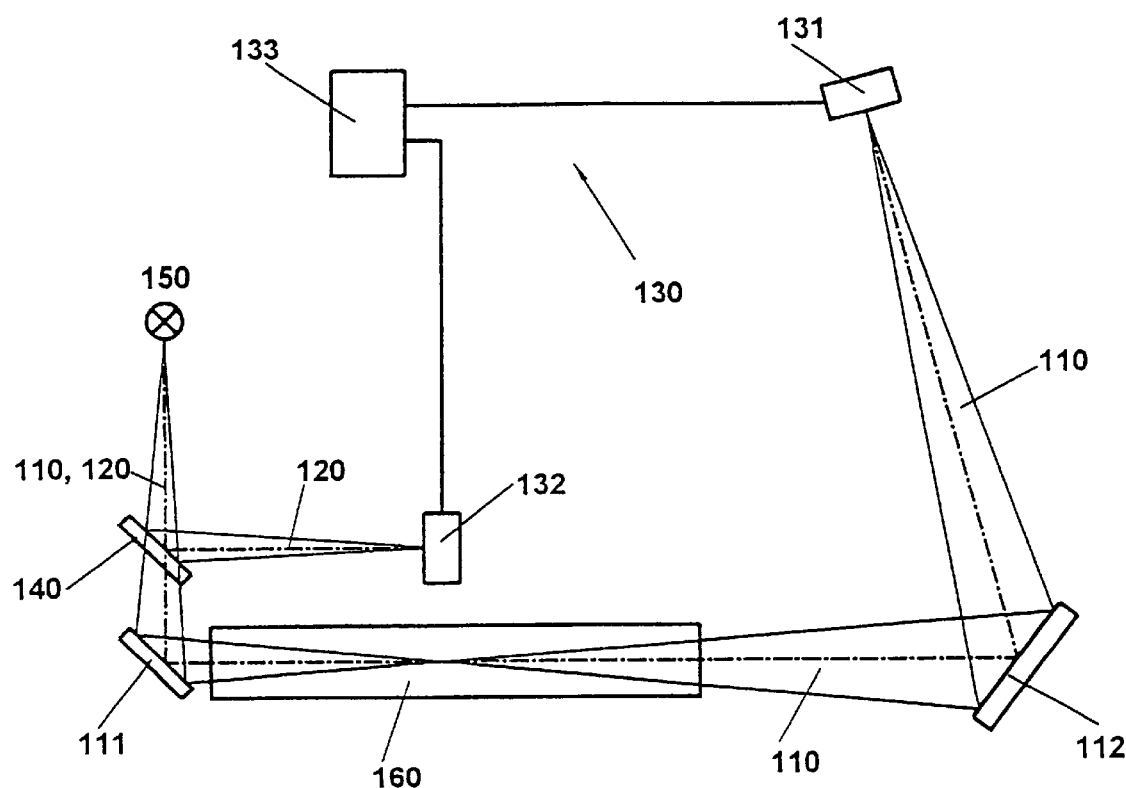
FIG. 1 shows an atomic absorption spectrometer in accordance with a first embodiment of the invention.

FIG. 1 shows an atomic absorption spectrometer 100 in accordance with a first embodiment of the present invention.

The atomic absorption spectrometer 100 comprises a measuring light path 110 and a reference light path 120.

The measuring light path 110 starts at a light source 150, emitting line radiation corresponding to an element which is to be detected in a sample to be analyzed. The light source 150 is a light source, as known in the field of atomic absorption. In the present embodiment, for example, a hollow cathode lamp is used as the light source 150.

Alternatively, other light sources known in the field of atomic absorption, as for example electrodeless discharge lamps, can be used.

A component of the line radiation emitted by the light source 150 travels in form of a measuring beam on the light measuring path 111 through a beam dividing means 140, and following, via a first optical element 111 into an atomization means 160 in which, when operated, the line radiation emitted by the light source 150 is absorbed in accordance with the concentration of the element to be detected.

This atomizing means 160 is schematically shown in FIG. 1. In accordance with the present invention, all atomizing means known in the field of atomic absorption spectroscopy, as for example an atomizing furnace, a flame or a cold vapor cell can be used.

Furthermore, the atomizing means 160 can be provided such that it comprises an atomization furnace, a flame and a cold vapor cell, which are provided on a support such that they can be selectively introduced into the measuring light path.

After passing the atomization means, the measuring beam is imaged from a second optical element 112 onto a detector element 131 of a detection means 130. In the embodiment shown in FIG. 1, a dispersion means (not shown) is provided in front of the detector 131, such that the radiation impinging onto the detector can be spatially resolved. For providing this detector element 131, a photodiode field or CCD detector may be used.

The optical elements 111 and 112 are provided in the embodiment shown in FIG. 1 in form of mirrors and are for redirecting the measuring light path. Further, also lenses for focusing the measuring light beam and/or the reference light beam can be employed. The optical element can be provided dependent on the arrangement of the light source, the atomizing means and the detector means.

The reference light path 120 starts, as the measuring light path 110, at the light source 150. The other component of the line radiation emitted from this light source is imaged by the beam dividing means 140 in the form of a reference beam onto a second detector element 132 of the detector means 130, with which the intensity of this reference beam can be detected. As in the case of the detector element 131, also this detector element 132 is provided with a dispersion means, in order to spatially resolve the radiation to be detected in dependence of the wavelength. As a detector element 132, a semiconductor, for example in the form of a photodiode array or a CCD detector can be used.

The beam dividing means 140 can be provided in the form of a semi-transparent plate. Further, the ratio with which the impinging radiation is divided has to be known. Preferably, the ratio can be set dependent on the absorption to be expected such that both the detector elements 131 and 132 operate in their optical range with respect to the signal of the noise ratio.

Further, the detector means 130 comprises an analyzing unit 133, which is advantageously provided in the form of a computer. In this analyzing unit, the intensity absorbed by the sample is determined from the intensities measured with the detector elements 131 and 132, and finally, the concentration of the element to be detected in the sample to be analyzed is determined from this intensity.

Figure 2:
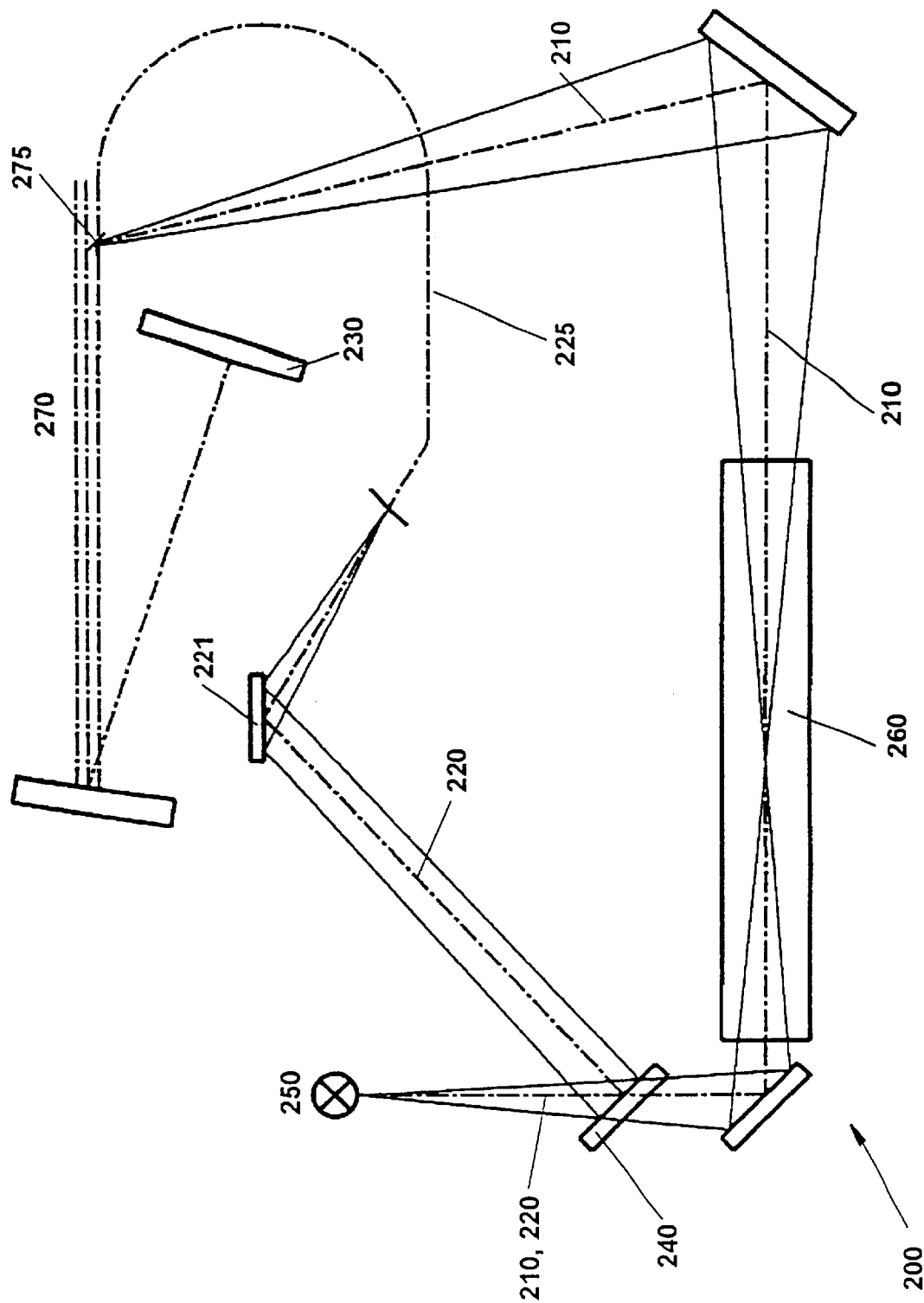
FIG. 2 shows an atomic absorption spectrometer in accordance with a second embodiment of the invention.

In FIG. 2, a further embodiment of an atomic absorption spectrometer 200 is shown. This atomic absorption spectrometer also comprises a light source 250, an atomization means 260, as well as a detector means 230.

The spectrometers shown in FIGS. 1 and 2 only differ in their detection means 130 and 230 and the guidance of the reference light paths 120 and 220. In the following, therefore, only the detection means 230 and the reference light path 220 will be discussed. With respect to the means, which are identical in both spectrometers, it is referred to the respective portions of the description of FIG. 1. In this context, it is to be pointed out that the reference numerals of corresponding elements differ only in their first digit.

Contrary to the detection means 130 in FIG. 1, the detection means 230 comprises a slit monochromator 270 with an entrance slit 275, onto which the measuring light beam and the reference light beam, displaced in longitudinal direction of the slit 275, are imaged.

Herein, the reference light beam travels, starting at the beam dividing means 240, via an optical element 221 and a light guiding connection 225 to the entrance slit 275 of the monochromator. As light guiding connection, known light guides, for example glass fibers of suitable material can be used. This arrangement, particularly using or the light guide connection enables a substantially more flexible reference light path 220 than possible, as for example with mirrors and lenses. Therefore, a smaller size for the spectrometer can be realized. Furthermore, adjusting the mirrors being necessary to image the reference beam exactly onto the entrance slit 275 can be avoided.

After the measuring radiation and the reference radiation have passed the monochromator, they impinge, spatially separated onto a detector element 231. As detector elements, semiconductor detectors in form of photodiode arrays of CCD detectors, can be used. However, it has to be insured, that the measuring radiation and the reference radiation can be measured separately from one another.

Figure 3:
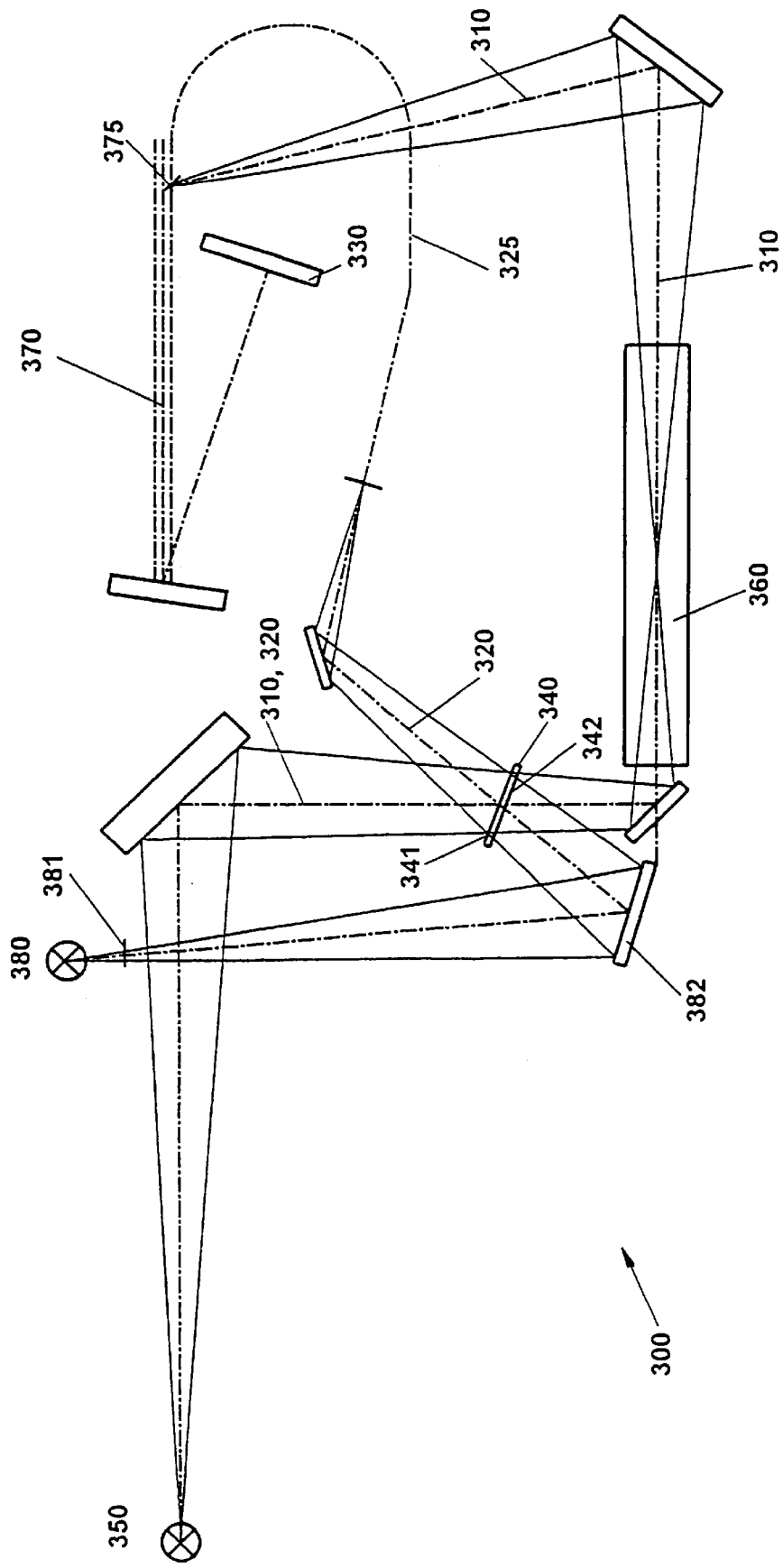
FIG. 3 shows an atomic absorption spectrometer in accordance with a third embodiment of the invention.

In FIG. 3, a further embodiment of an atomic absorption spectrometer 300 in accordance with the present invention is shown.

This spectrometer 300 differs from the one shown in FIG. 2 in that, additionally, means for performing a D2-correction of the absorption measurement is provided. In the following, therefore, only this difference will be described. For the description of the remaining components, it is referred to the respective portions of the description of FIG. 2, and FIG. 1, respectively. The reference numerals have been chosen such that reference numerals of corresponding components differ only in their first digit.

For a D2 correction of the absorption, a light source 380 is provided in the form of a D2-lamp emitting continuum radiation.

The continuum radiation emitted from the light source 380 impinges, via an optical element 382 onto the beam divider means 340. There, the radiation is, as the line radiation emitted by the line radiation source 350, separated into a measuring beam and a reference beam. After the beam dividing means 340, the light paths for the continuum radiation and the line radiation (as seen from the respective light sources 380 and 350, respectively) are identical. Therefore, the continuum measuring beam, after having passed through the atomization means 360, and the continuum's reference beam are imaged spatially separated onto the entrance slit 375 of the monochromator and finally, onto the detection means 330.

Attenuating means 381 is provided in front of the continuum light source 380. This attenuating means can be provided in form of an absorption grating or an transmission filter. Through the grating, and the transmission, the intensity of the continuum light source can be adapted to the intensity of the line light source.

Alternatively to the attenuating means 381, a beam divider 340 can be used in the arrangement shown in FIG.

3 for adapting the intensity of the continuum light source to the intensity of the line light source. With this, the beam divider has to have a reflection/transmission ratio being unequal to one. Since the line radiation and the continuum's radiation in the arrangement shown in FIG. 3 is coupled into the beam divider on opposing sides, and assuming a reflection/transmission of 40:60, then 60% of the line radiation impinging on the side 341 are passing through into the measuring light path. On the other hand, the beam divider reflects 30% of the continuum light into the measuring light path on the other side 342.

A further possibility to adapt the intensity of the continuum's light source is controlling the light sources itself. With this, the energy supply to the light source or the integration time for the measurement can be changed.

Here, changing the integration time which will be described in connection with the methods of the present invention is the most advantageous adaptation of the continuum light source to the line light source. In particular, a controlling of the light sources can be performed without rearranging the spectrometer, i.e. without exchanging the beam divider means and/or the attenuation means. Further, and in particular in contrast to using an attenuation means, the entire emitted continuum radiation can be used, whereby an efficient usage of the light source is ensured. Thus, changing the integration time is the most flexible adaptation of the D2 light source to the line light source.

Figure 4:
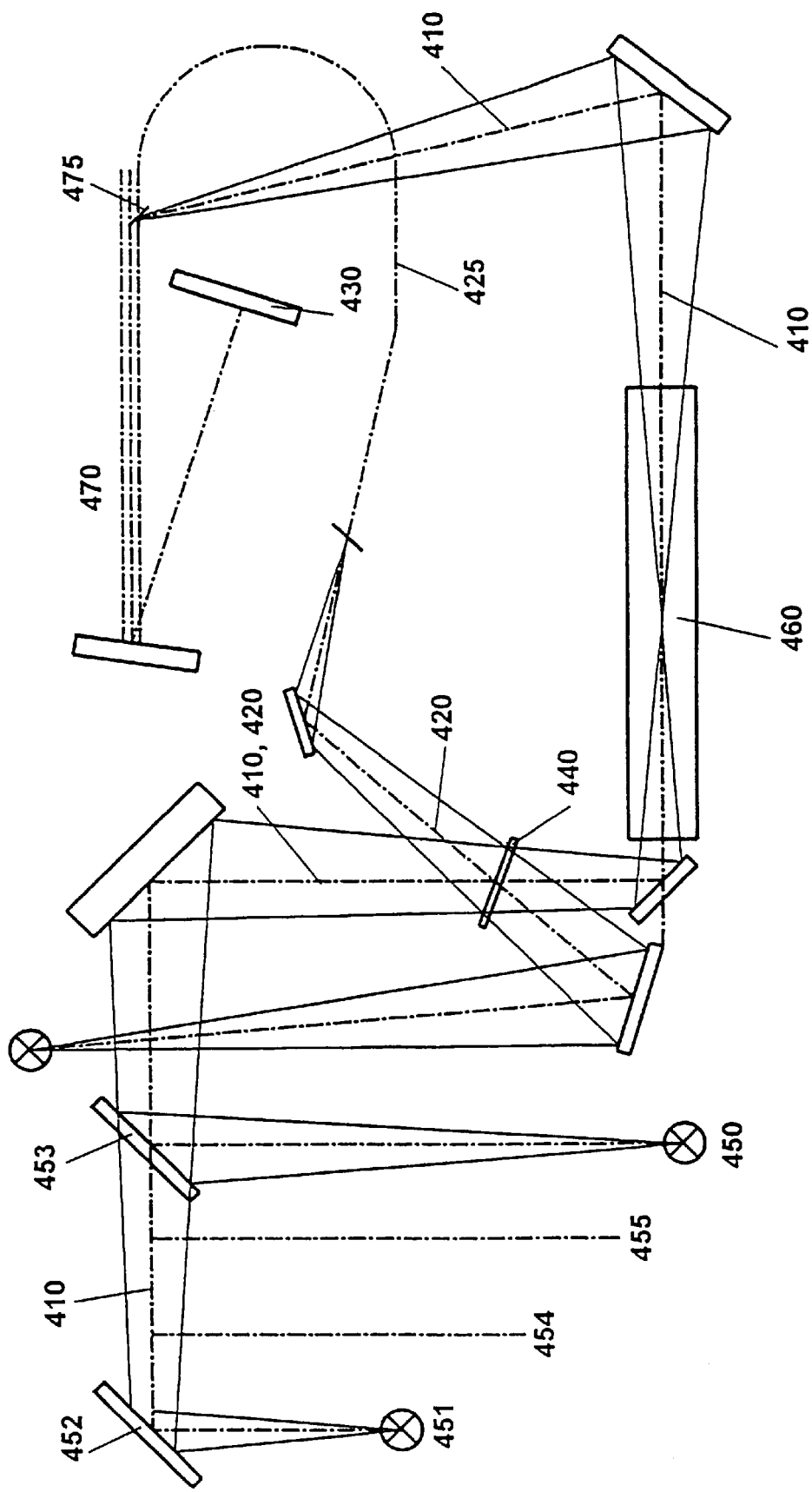
FIG. 4 shows an atomic absorption spectrometer in accordance with a fourth embodiment of the invention.
Figure 5A:
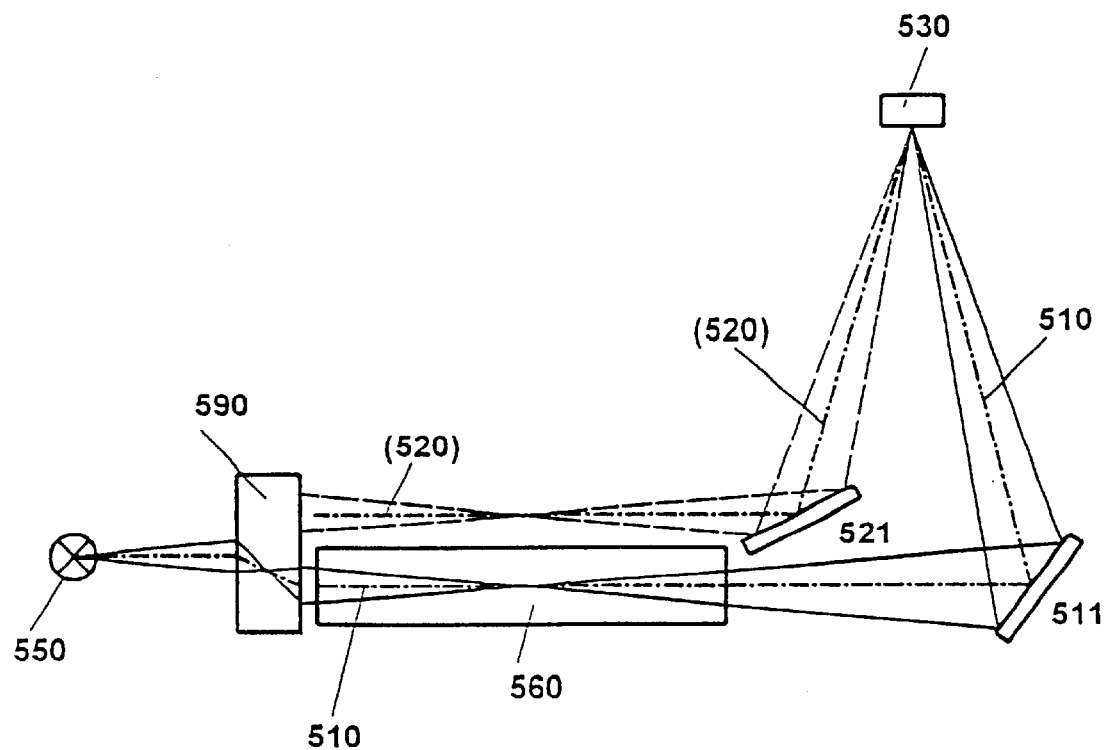
FIGS. 5A and 5B show an atomic absorption spectrometer in accordance with the prior art.
Figure 5B:
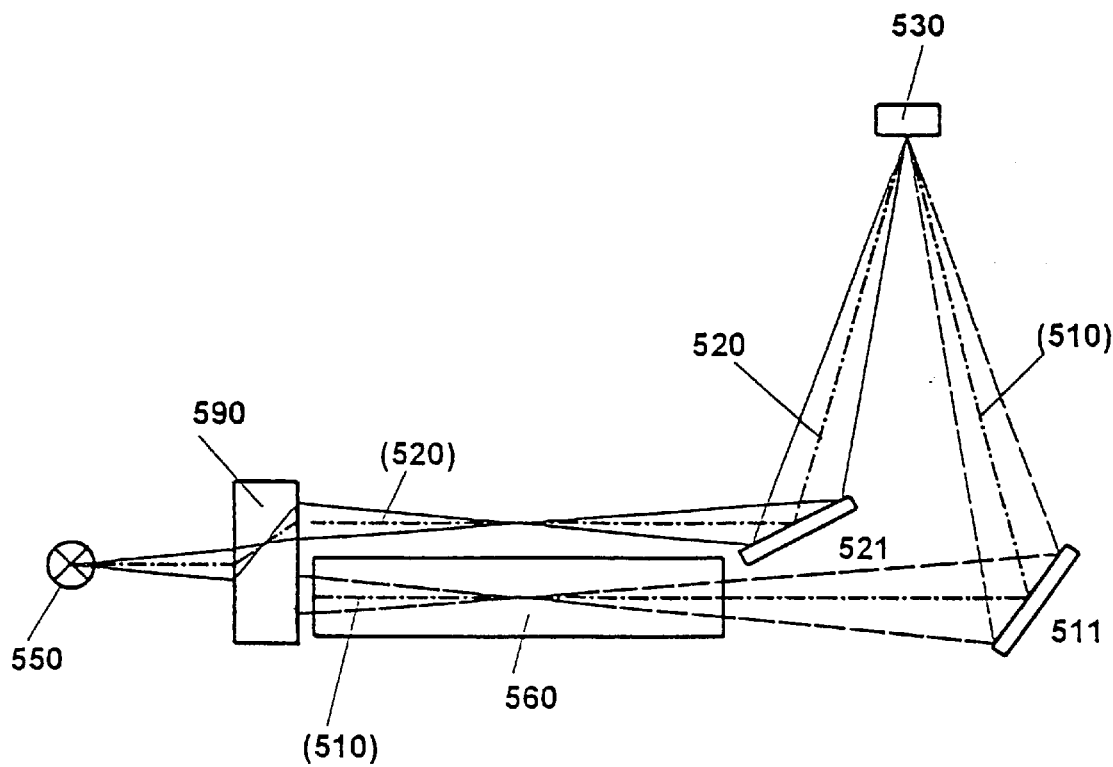

FIG. 4 shows a further embodiment of an atomic absorption spectrometer 400 in accordance with the present invention. This atomic absorption spectrometer differs from the one shown in FIG. 3 only in that a further light source 451 is provided, said light source emitting a line radiation corresponding to a further element to be detected contained in the sample to be analyzed. For the description of the remaining components, therefore, it is referred to the respective sections of FIG. 3, FIG. 2, and FIG. 1, respectively. Here, the reference signs have been chosen such that the different signs of corresponding components differ only in their first digit.

The line radiation of this light source 451 is redirected via an optical element 452 and coupled into the measuring light path and the reference light path, respectively, via a further optical element 453.

Furthermore, it is indicated in FIG. 4 by the reference numerals 454 and 455 that, if need be, further light sources for emitting a line radiation can be provided.

In the following, a method for performing a double-beam atomic absorption in accordance with a first embodiment of the present invention will be described.

This method can be performed with an atomic absorption spectrometer in accordance with one of the above discussed embodiments of the present invention. In the following, this method will be described referring to the atomic absorption spectrometer in accordance with FIG. 1. In the method, a component of the radiation from a light source 150 emitting line radiation of an element to be detected is coupled into the measuring light path 110, which leads from the light source through an atomization means 160 for atomizing a sample containing the element to be detected, to a detecting means 130.

By means of the beam splitting 140, the remaining component of the radiation from the light source 150 is coupled into a reference light path, leading from the light source 150 directly to the detection means 130.

Finally, with the detection means 130, the intensity of the radiation passed through the measuring light path, and the intensity of the radiation, passed through the reference light path, is measured.

From the intensity of the radiation passed through the measuring light path, and the radiation passed through the reference light path, finally, the intensity of the radiation absorbed by the atomized sample will be determined.

Figure 6:
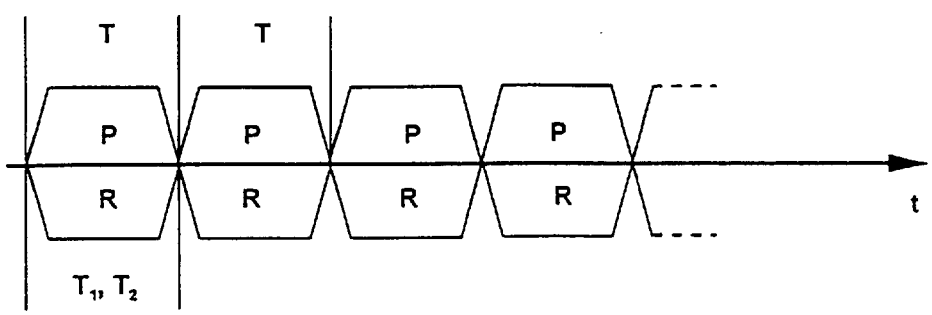
FIG. 6 shows diagram of a time sequence of a method for performing a double-beam atomic absorption in accordance with a first embodiment of the invention.
Figure 14:
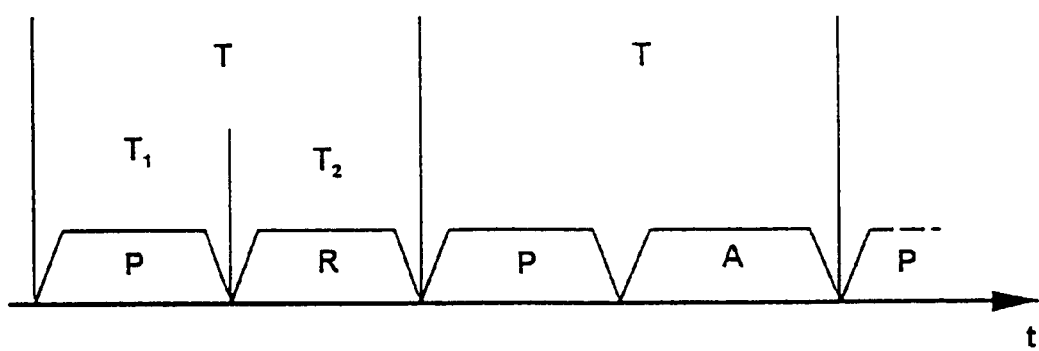
FIG. 14 shows a diagram of a time sequence of a method for performing a double-beam atomic absorption in accordance with the prior art.

FIG. 6 shows a time sequence diagram representing the above described method. Analog to FIG. 14 in which a time sequence diagram of a method in accordance with the prior art is given, FIG. 6 shows several measuring cycles T. Also the indications of the phases are chosen analog to FIG. 14. Thus, P represents the sample measurement and R represents the reference measurement. In accordance with FIG. 6, the measuring times $T_P$ and $T_R$ take the same value.

As can be seen in FIG. 6, in the method in accordance with the invention, the sample measurements and the reference measurements are performed simultaneously. Therefore, and in contrast to the method described in connection with FIG. 14 in which the time for a cycle is $T=T_T+T_R$, the time for the cycle can be reduced to $T=T_R=T_P$.

In the following, a method for performing a double-beam atomic absorption in accordance with the second embodiment of the invention is described.

In this method, additionally, a so call D2-correction, i.e. a correction of the background, is performed. Thus, for performing this method, an atomic absorption spectrometer is required, with which a D2-correction can be performed. For doing so, the atomic absorption spectrometer as shown in FIG. 3 or FIG. 4 is sufficient. In the following, the method will be described referring to the atomic absorption spectrometer in accordance with FIG. 3.

Contrary to the above described first method, radiation from a continuum light source 380 is coupled by means of a beam splitter 340 in both the measuring light path 310 and the reference light path 320. With a detection means 330, the intensity of the continuum radiation passed through the measuring light path, and the intensity of the continuum radiation passed through the reference light path is simultaneously measured.

Then, from the intensity of the continuum radiation passed through the measuring light path and the intensity of the continuum radiation passed through the reference light path, the continuum radiation absorbed by the atomized sample is determined, and the line radiation absorbed by the sample is corrected with the continuum radiation absorbed by the sample.

Figure 7:
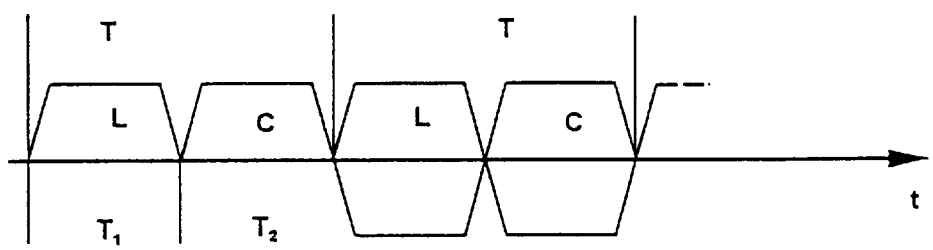
FIG. 7 shows diagram of a time sequence of a method for performing a doublebeam atomic absorption in accordance with a second embodiment of the invention.

FIG. 7 shows a time sequence diagram of measuring the line radiation and the continuum radiation in accordance with this method. This time sequence diagram shows several measuring cycles, each having a cycle time T.

In a first phase L of the measuring cycle, the measurement of the line radiation passed through the measuring light path and the reference light path is performed simultaneously. With this, the measuring time is $T_L$.

In a second phase C of the measuring cycle, the continuum radiation passed through the measuring light path and the reference light path is measured. With this, the measuring time is $T_C$.

The measuring times $T_L$ and $T_C$ are set in this method dependent on the intensity of the radiation sources, on the sample matrix and the element contained in the sample, such that an optimal signal to noise ratio results.

In the following, a method for performing a double-beam atomic absorption in accordance with the third embodiment of the invention is described.

In comparison to the second above described method, in this method, the radiation emitted by the atomic absorption means is additionally taken into consideration. This radiation can occur, for example, in an atomizing furnace or a flame, in form of a temperature radiation. Furthermore, this radiation can be produced by physical processes, as for example, spontaneous emission of the elements taking part in the atomization.

For performing this method, and as in the second method, the atomic absorbing spectrometers described in FIGS. 3 and 4 can be used.

The third method differs from the second method in that, additionally, to the steps performed in the second method, also the radiation is measured which impinges on the detection means during so called dark phases, in which neither radiation from the light source emitting line radiation, nor the light source emitting continuum radiation is measured.

Figure 8:
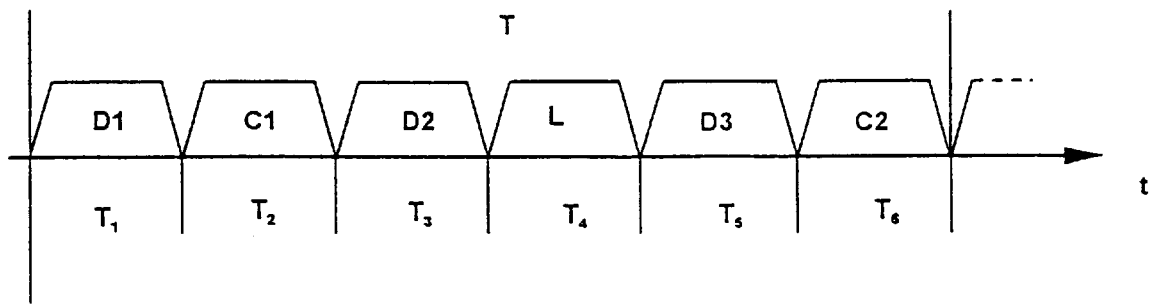
FIG. 8 shows diagram of a time sequence of a method for performing a doublebeam atomic absorption in accordance with a third embodiment of the invention.

In FIG. 8, a time sequence diagram of this method is shown. As FIGS. 6 and 7, FIG. 8 shows a measuring cycle T. This measuring cycle comprises the following time dependent sequence, a first measurement of the radiation emitted by the atomizing means D1 (so called dark phase), a first measurement of the continuum radiation C1, a second measurement of the radiation emitted by the atomizing means D2, a measurement of the line radiation L, a third measurement of the radiation emitted by the atomizing means, and a second measurement of the continuum radiation D2.

The single measurements are performed for a certain time interval. In particular, and with this the measuring time $T_1$ for the first measurement of the radiation emitted by the atomizing means D1, the measuring time $T_2$ for the first measurement of the continuum's radiation C1, the measuring time $T_3$ for the second measurement of the radiation emitted by the atomizing means D2, the measuring time $T_4$ for the measurement of the line radiation L, the measuring time $T_5$ for the third measurement of the radiation emitted by the atomizing means D3, and the measuring time $T_6$ for the second measurement of the continuum's radiation C2 are set dependent on the used atomizing process, on the intensity of the light source emitting the line radiation and the intensity of the light source for emitting the continuum radiation, on the intensity of the radiation produced by the atomizing means, as well as on the changing rate of the background absorption.

With this, the measuring times are optimized such that, having measuring time as short as possible, an optical correction value is obtained for both the D2-correction as well as the correction with respect to the radiation emitted by the atomizing means.

In the following, and referring to FIGS. 9 to 13, five examples of an optimal time controlling for performing the methods according to the third embodiment of the present invention are described.

EXAMPLE 1

In this example, the atomizing means comprises an atomizing furnace. The atomic absorption spectrometer has been operated under standard conditions. An operation of the atomizing furnace under standard conditions is for example, suited to detect Beryllium in alloys.

Figure 9A:
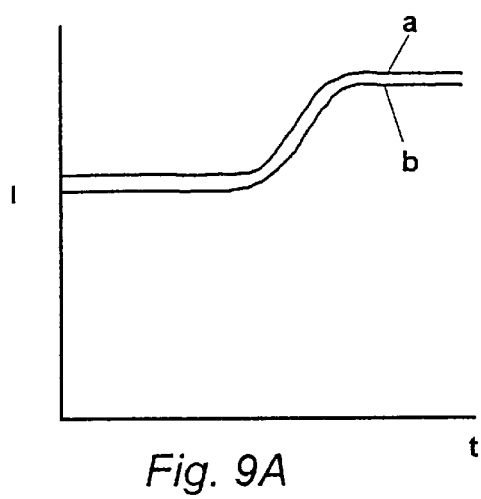
FIGS. 9A, 9B, and 9C show a first example of a time controlling process for the method in accordance with the third embodiment of the invention.

As can be seen from FIG. 9A, in which the intensity I (y-axis) is shown in dependency on the time t (x-axis), the upper curve a being the intensity of the line radiation source (including emission), and the lower curve b being the intensity of the continuum radiation source (including emission), the intensities of the light source for the line radiation and for the continuum radiation have the same order of magnitude. Further, the radiation emission of the furnace was smaller than the intensity of the light sources.

Figure 9B:
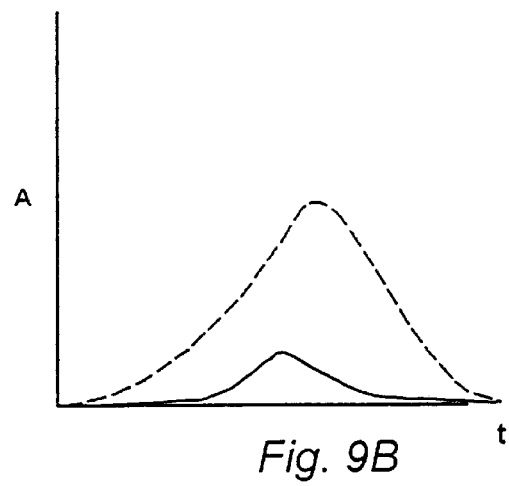

FIG. 9B, representing absorbance (y-axis) against time (x-axis), shows the absorbance of the atomic absorption (solid curve) and of the background (dashed curve). As can be seen in this Figure, the absorbance of the background has only changed moderately in comparison to the absorbance of the atomic absorption.

Figure 9C:
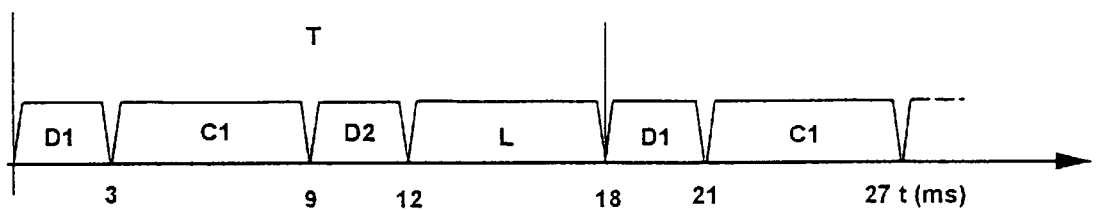

An optimization of the third method yields, for the above standard conditions, the measuring cycle shown in FIG. 9C. In accordance with FIG. 9C, the following measuring times result for the single phases:

$T_1$: 3 ms (D1)
$T_2$: 6 ms (C1)
$T_3$: 3 ms (D2)
$T_4$: 6 ms (L)
$T_5$: 0 ms (D3)
$T_6$: 0 ms (C2)

It can be read from these optimized measuring times that, due to the moderate change in the absorption of the background, only one continuum measurement is required per cycle.

The corrected line radiation for this measuring cycle is obtained as follows:

The mean value of the dark phase measurements D1 and D2 is used to correct the continuum measurement C1. The measurement of the dark phase measurements A2 and D1 of the succeeding cycle is used to correct the line measurement L. Finally, the mean value of two continuum measurements C1, which have been corrected with the dark phase measurement, is used to correct L. The time between the measurements was 18 ms.

EXAMPLE 2

Figure 10A:
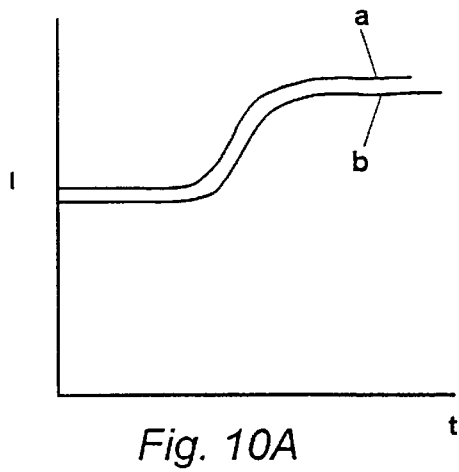
FIGS. 10A, 10B, and 10C show a second example of a time controlling process for the method in accordance with the third embodiment of the invention.

In this example, an atomizing furnace has been used as atomizing means. As can be seen from FIG. 10A showing the intensities I (y-axis) dependent on the time t (x-axis), the upper curve a representing the intensity of the light radiation source (including emission) and the lower curve b representing the intensity of the continuum's radiation source (including emission), also in this example, the intensities of the light source for the line radiation and for the continuum radiation were in the same order of magnitude. The emission from the furnace was relatively high in comparison to the light source intensifies.

Figure 10B:
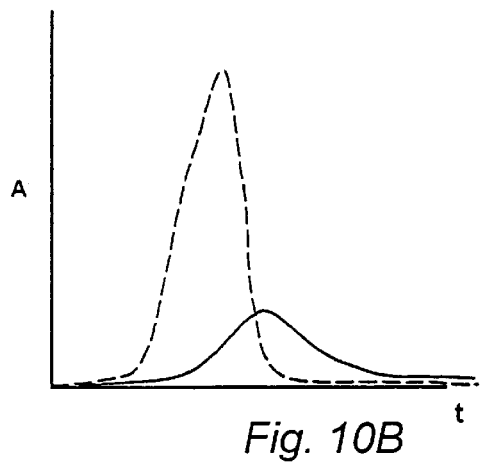

Furthermore, the absorbance of the background (dashed curve) has changed relatively strong in comparison to the absorbance of the atomic absorption (solid curve), as shown in FIG. 10B, which shows, according to FIG. 9B, the absorbance A (y-axis) in dependence on the time t (x-axis).

Using an atomization furnace under the above described conditions, is particularly suitable for detecting. Beryllium in biological samples, for example blood and the like.

Figure 10C:
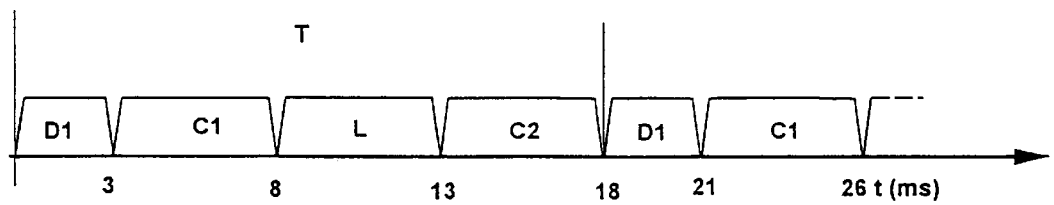

An optimization of the third method for these conditions yields the measuring cycle as shown in FIG. 10C. In accordance with FIG. 10C, the following measuring times result for the single phases of the measuring cycle:

T: 18 ms
$T_1$: 3 ms (D1)
$T_2$: 5 ms (C1)
$T_3$: 0 ms (D2)

$T_4$: 5 ms (L)
$T_5$: 0 ms (D3)
$T_6$: 5 ms (C2)

It can be seen from these optimized measuring times, both continuum measurements have to be performed, contrary to example 1, due to the strong change of the absorbance of the background.

The corrected line radiation for this measuring cycle is obtained as follows:

The mean value of the dark phase measurements D1 of two succeeding measuring cycles is used to correct the measurement C1, L and C2. Then, the mean value of the continuum measurements C1 and C2, both having been corrected with the dark phase measurement, are used to correct L. The time between the measurements was 10 ms.

EXAMPLE 3

In this example an atomization furnace has been used. As can be seen from FIG. 11A, in which according to FIGS. 9A and 10A, intensities I (y-axis) are shown dependent on time t (x-axis), the upper curve a representing the intensity of the continuing radiation source (including emission) and the lower curve b representing the intensity of the line radiation source (including emission), the intensity of the light source for the line radiation was considerably smaller than the intensity for the continuum radiation. Further, the radiation emission of the furnace was small in comparison to the intensities of the light sources.

Figure 11A:
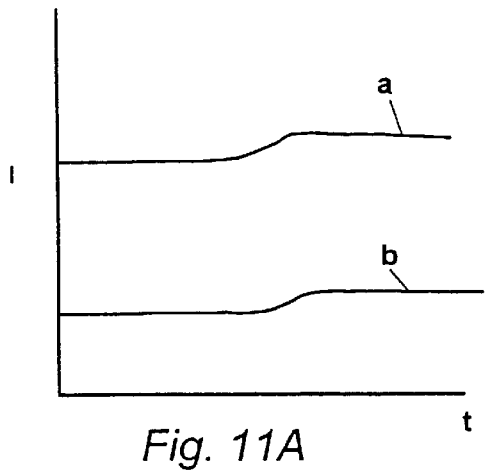
FIGS. 11A, 11B, and 11C show a third example of a time controlling process for the method in accordance with the third embodiment of the invention.
Figure 11B:
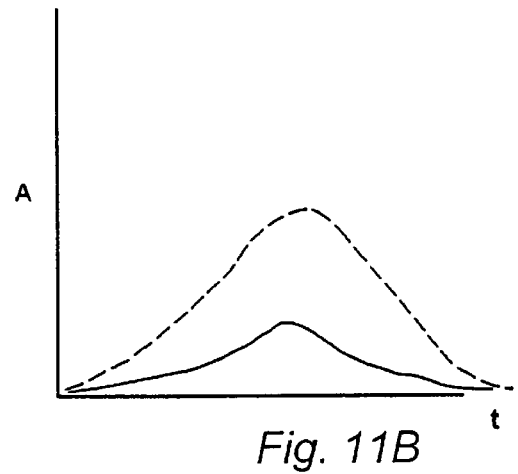

As can be seen from FIG. 11B, in which according to FIGS. 9B and 10B, the absorbance A (y-axis) is shown dependent on the time t (x-axis), in this example, the absorbance of the background has only changed moderately in comparison to the absorbance of the atomic absorption.

Using an atomization furnace under these conditions is particularly suitable to detect arsenic in biological samples, for examples blood and the like.

Figure 11C:
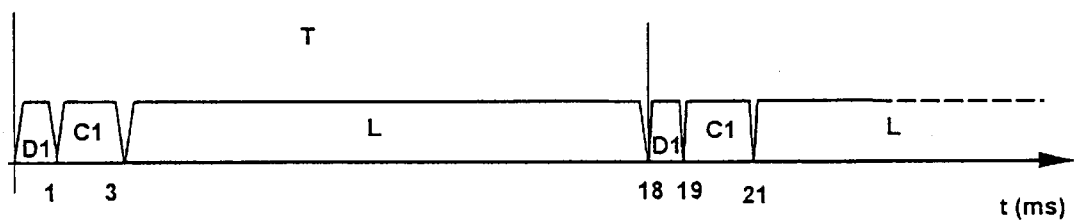

An optimization of the third method for these conditions yields the measuring cycle shown in FIG. 11C. In accordance with FIG. 11C the following measuring times result for the single phases of the measuring cycle:

T: 18 ms
$T_1$: 1 ms (D1)
$T_2$: 2 ms (C1)
$T_3$: 0 ms (D2)
$T_4$: 15 ms (L)
$T_5$: 0 ms (D3)
$T_6$: 0 ms (C2)

As can be seen from the optimized measuring times of the above mentioned conditions, a comparably large measuring time for the line radiation has to be adopted due to the small intensity of the line radiation source.

In comparison to example 1, the integrated intensity for the line light source has been increased by a factor of 2.5.

The background absorption only changing moderately, it is sufficient to perform one continuum measurement per cycle. The same is true for the dark phase measurement.

The correct line radiation is obtained for this measuring cycle as follows:

The mean value of the dark phase measurements D1 of two succeeding measuring cycles is used to correct the measurements C1. Then, the mean value of the continuum measurements C1 of two succeeding cycles, both being corrected with the dark phase measurements, is used to correct L. The time between the measurements was 18 ms.

EXAMPLE 4

In this example a flame has been used as atomization means. The change of the absorption constance in this example was relatively slow. The intensity of the line radiation source was relatively low.

Using a flame as atomization means is suitable, for example, for detection of calcium in water.

Figure 12:
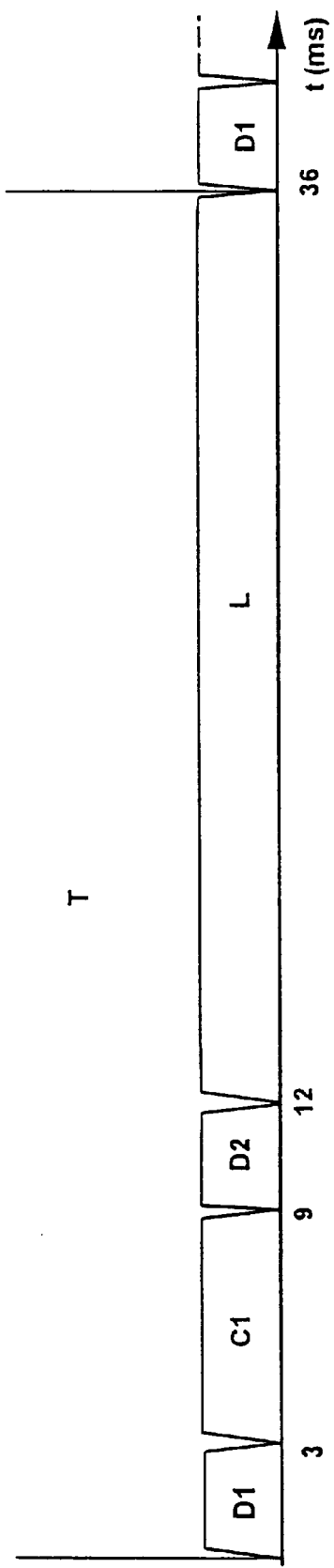
FIG. 12 shows a fourth example of a time controlling process for the method in accordance with the third embodiment of the invention.

Optimization of the third method yields, for the above conditions, the measuring cycle shown in FIG. 12. In accordance with FIG. 12, the following measuring times result for the single phases of the measuring cycles:

T: 36 ms
$T_1$: 3 ms (D1)
$T_2$: 6 ms (C1)
$T_3$: 3 ms (D2)
$T_4$: 24 ms (L)
$T_5$: 0 ms (D3)
$T_6$: 0 ms (C2)

The longer integration time for the line measurements reduces, in this example, the amount of the detector read-out noise. Therefore, the overall signal to noise ratio is improved.

The corrected line radiation for this measuring cycle is obtained as follows: The mean value of the dark phase measurements D1 and D2 is used to correct the continuum measurement C1. The mean value of the dark phase measurements D2 and D1 of the succeeding cycle is used to correct the line measurement L. Finally, the mean value of two continuum measurement C1, having been corrected with the dark phase measurement, are used to correct L.

EXAMPLE 5

In this example a cold vapor cell has been used as atomizing means. The change in the absorption constance in this example was, as in example 4, relatively slow. The intensity of the line radiation sources was relatively low.

Using a cold vapor cell under the above mentioned conditions, is particularly suitable for detecting mercury, for example biological samples.

Figure 13:
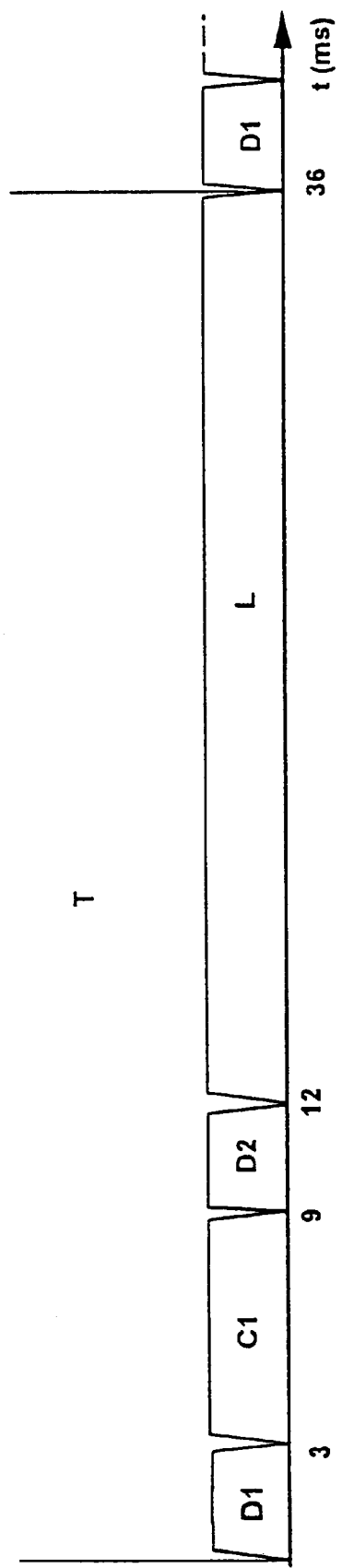
FIG. 13 shows a fifth example of a time controlling process for the method in accordance with the third embodiment of the invention.

An optimization of the third method for these conditions yields the measuring cycle shown in FIG. 13. In accordance with FIG. 13, the following measuring times result for the single phases of the measuring cycle:

T: 36 ms
$T_1$: 3 ms (D1)
$T_2$: 6 ms (C1)
$T_3$: 3 ms (D2)
$T_4$: 24 ms (L)
$T_5$: 0 ms (D3)
$T_6$: 0 ms (C2)

The longer integration time for the line measurement reduces, also in this example, the relative amount of detector read-out noise. Therefore, the overall signal to noise ratio is improved.

The corrected line radiation for this measuring cycle is obtained as follows:

The mean value of the dark phase measurements D1 and D2 is used to correct the continuum measurement C1. The mean value of the dark phase measurements D2 and D1 of the succeeding cycle is used to correct the line measurement L. Finally, the mean value of two continuum measurements C1 being corrected with the dark phase measurement is used to correct L.

We claim:

1. An atomic absorption spectrometer (100; 200; 300; 400), comprising:

a plurality of light sources including at least one light source (150; 250; 350; 450, 451) emitting line radiation corresponding to at least one element to be detected and a continuum light source (380; 480) emitting continuum radiation for background correction;

a measuring light path (110; 210; 310; 410) leading from said plurality of light sources, through an atomization means (160; 260; 360; 460) for atomizing a sample containing the element to be detected, to a detection means (130; 230; 330; 430), a reference light path (120; 220; 320; 420) leading from said plurality of light sources to the detection means (130; 230; 330; 430), a beam splitting means (140; 240; 340; 440) for simultaneously guiding a first component of radiation from said plurality of light sources along the measuring light path (110; 210; 310; 410), and a second component of radiation from said plurality of light sources along the reference light path (120; 220; 320; 420); and, a control means (190; 290; 390; 490) for time dependently controlling the intensity of each of said plurality of light sources such that each of said plurality of light sources is activated alternately in a predetermined sequence.

2. Atomic absorption spectrometer according to claim 1 wherein the detection means comprises a first detector (131) for detecting the first component of the line radiation, and a second detector (132) for detecting the second component of the line radiation.

3. Atomic absorption spectrometer according to claim 1, wherein the detection means comprises a detector (230; 330; 430), comprising at least two sections, the first section thereof being provided for detecting the first component of the component.

4. Atomic absorption spectrometer according to claim 2, wherein the at least one light source (150; 250; 350; 450, 451) comprises a hollow cathode lamp or an electrodeless discharge lamp.

5. Atomic absorption spectrometer according to claim 4, wherein a monochromator means (270; 370; 470) is provided in front of said first detector and said second detector.

6. Atomic absorption spectrometer in accordance with claim 5, wherein the monochromator means (270; 370; 470) comprises an entrance slit (275; 375; 475), and the first and the second component of the line radiation are imaged onto the entrance slit such that they are separated from each other in longitudinal direction of the entrance slit.

7. Atomic absorption spectrometer according to claim 6, in which the second component of the line radiation is guidable via a light guiding means (225; 325; 425) from the beam splitting means (140; 240; 340; 440) to the entrance slit (275; 375; 475) of the monochromator means (270; 370; 470).

8. Atomic absorption spectrometer in accordance with claim 2 wherein a polychromator means is provided in front of the or each detector.

9. Atomic absorption spectrometer in accordance with claim 1, wherein said detection means is provided in form of at least one semiconductor detector.

10. Atomic absorption spectrometer in accordance with claim 9, wherein said semiconductor detector is provided in form of a photodiode detector or a CCD detector.

11. Atomic absorption spectrometer in accordance with claim 1, wherein the atomization means (160; 260; 360; 460) comprises an atomization furnace.

12. Atomic absorption spectrometer in accordance with one of the claim 1, wherein the atomization means (160; 260; 360; 460) comprises a flame or a cold vapor cell.

13. Atomic absorption spectrometer in accordance with claim 1, wherein the atomization means (160; 260; 360; 460) comprises an atomization furnace and/or a flame and/or a cold vapor cell being selectively introducable into the measuring light path.

14. Atomic absorption spectrometer in accordance with claim 13, wherein the atomization means (160; 260; 360; 460) are micro-processor controllably introducable into the measuring light path.

15. Atomic absorption spectrometer in accordance with claim 1, wherein the continuum light source (380; 480) comprises a D2-lamp.

16. Method for performing a double-beam atomic absorption, comprising the steps of:

providing a plurality of light sources including at least one light source emitting line radiation corresponding to at least one element to be detected and a continuum light source emitting continuum radiation for background correction;

coupling radiation of said at least one light source into a measuring light path, leading from said plurality of light sources through an atomization means for atomizing a sample containing the element to be detected, to a detecting means, coupling of radiation of said at least one light source into a reference light path, leading from said plurality of light sources to the detection means, simultaneously measuring the intensity of the radiation passed through the measuring light path and the intensity of the radiation passed through the reference light path, determining the radiation absorbed by the atomized sample from the intensity of the radiation passed through the measuring light path and the intensity of the reference light path, coupling radiation of a continuum light source into the measuring light path and into the reference light path, simultaneously measuring the intensity of the continuum radiation passed through the measuring light path and the intensity of the continuum radiation passed through the reference light path, determining the background radiation absorbed by the atomized sample from the intensity of the continuum radiation passed through the measuring light path and the intensity of the continuum radiation passed through the reference light path, and, correcting the line radiation absorbed by the sample by means of the background radiation absorbed by the sample.

17. Method in accordance with claim 16, wherein the simultaneously measuring of the intensity of the line radiation passed through the measuring line path and the intensity of the line radiation passed through the reference line path, as well as the simultaneously measuring the intensity of the continuum radiation passed through the measuring light path and the intensity of the continuum radiation passed through the reference light path are performed in accordance with the measuring cycle (D) comprising a measurement of the continuum radiation (C) and a measurement of the line radiation (L).

18. Method in accordance with claim 17, wherein the measuring time for measuring the continuum radiation (C) and the measuring time for measuring the line radiation (L) are set dependent on the used atomization process, on the intensity of the line radiation and the intensity of the continuum radiation source, as well as on the changing rate of the background absorption.

19. Method in accordance with claim 16, wherein the radiation is measured which has been emitted by the atomization means during dark phases, in which neither radiation from the line radiation emitting light source nor from the line radiation emitting light source and the continuum radiation emitting light source is emitted.

20. Method in accordance with claim 19, wherein the simultaneously measuring of the intensity of the line radiation, the simultaneously measuring of the intensity of the continuum radiation and the measuring of the intensity of the radiation emitted by the atomization means are performed in accordance with a measuring cycle, comprising a first measurement of the radiation emitted by the atomization means (D1), a measurement of the continuum radiation (C1), a second measurement of the radiation emitted by the atomization means (D2), a measurement of the line radiation (L), a third measurement of the radiation emitted by the atomization means (D3) and a second measurement of the continuum radiation (C2).

21. Method in accordance with claim 20, wherein the measuring time ($T_1$) for the first measurement of the radiation emitted by the atomization means (D1), the measuring time ($T_2$) for the first measurement of the continuum radiation (C1), the measuring time ($T_3$) for the second measurement of the radiation emitted by the atomizing means (D2), the measuring time ($T_4$) for the measurement of the line radiation (L), the measuring time ($T_5$) for the third measurement of the radiation emitted by the atomizing means (D3), and the measuring time ($T_6$) for the second measurement of the continuum radiation (C2) are set dependent on the used atomization process, on the intensity of the line radiation source and the intensity of the continuum radiation source, on the intensity of the radiation produced by the atomizing means, as well as on the changing rate of the background absorption.

* * * * *